(12) United States Patent
Masto et al.

(10) Patent No.: US 11,026,883 B2
(45) Date of Patent: Jun. 8, 2021

(54) LYOPHILIZED PHARMACEUTICAL COMPOSITIONS FOR VAGINAL DELIVERY

(71) Applicant: Catalent U.K. Swindon Zydis Limited, Swindon (GB)

(72) Inventors: Emilie Masto, Swindon (GB); Lisa Garrett, Swindon (GB); Niamh Barrat, Swindon (GB); Yik Teng Wong, Swindon (GB); Rosaleen Theresa McLaughlin, Swindon (GB); Susan Gerrard Banbury, Swindon (GB)

(73) Assignee: Catalent U.K. Swindon Zydis Limited, Glasgow (GB)

( * ) Notice: Subject to any disclaimer, the term of this patent is extended or adjusted under 35 U.S.C. 154(b) by 0 days.

(21) Appl. No.: 16/341,808

(22) PCT Filed: Oct. 13, 2017

(86) PCT No.: PCT/IB2017/056373
§ 371 (c)(1),
(2) Date: Apr. 12, 2019

(87) PCT Pub. No.: WO2018/069888
PCT Pub. Date: Apr. 19, 2018

(65) Prior Publication Data
US 2019/0314274 A1 Oct. 17, 2019

Related U.S. Application Data

(60) Provisional application No. 62/407,709, filed on Oct. 13, 2016.

(51) Int. Cl.
*A61K 9/00* (2006.01)
*A61K 9/20* (2006.01)
*A61K 31/522* (2006.01)

(52) U.S. Cl.
CPC ............ *A61K 9/0036* (2013.01); *A61K 9/205* (2013.01); *A61K 9/2009* (2013.01);
(Continued)

(58) Field of Classification Search
None
See application file for complete search history.

(56) References Cited

U.S. PATENT DOCUMENTS

| 4,371,516 A | 2/1983 | Gregory et al. |
| 4,642,903 A | 2/1987 | Davies |

(Continued)

FOREIGN PATENT DOCUMENTS

| CN | 1224381 C | 10/2005 |
| CN | 102784120 A | 11/2012 |

(Continued)

OTHER PUBLICATIONS

Basic Principles of Freeze Drying (SP Scientific, Nov. 2, 2010) (Year: 2010).*

(Continued)

*Primary Examiner* — Melissa S Mercier
(74) *Attorney, Agent, or Firm* — Morrison & Foerster LLP

(57) ABSTRACT

Disclosed herein is a solid lyophilized vaginal dosage form that can have an effective amount of at least one active ingredient, a crystalline structure forming agent in an amount of about 5 wt. % to about 40 wt. %, based on the total weight of the lyophilized dosage form, and at least one polymeric mucoadhesive matrix forming agent. The dosage form can have a pH of about 4.0 to 5.0, and can disintegrate within 120 seconds after being contacted with a vaginal mucosa. A method of delivering an active ingredient to the vaginal mucosa using the disclosed solid dosage form is also described.

21 Claims, 12 Drawing Sheets

(52) U.S. Cl.
CPC .......... *A61K 9/2018* (2013.01); *A61K 9/2031* (2013.01); *A61K 9/2036* (2013.01); *A61K 9/2054* (2013.01); *A61K 9/2059* (2013.01); *A61K 9/2063* (2013.01); *A61K 9/2072* (2013.01); *A61K 31/522* (2013.01)

(56) References Cited

U.S. PATENT DOCUMENTS

| | | | |
|---|---|---|---|
| 5,178,878 A | | 1/1993 | Wehling et al. |
| 5,417,224 A | * | 5/1995 | Petrus ................. A61F 6/08 128/833 |
| 5,866,163 A | | 2/1999 | Myers et al. |
| 5,976,577 A | | 11/1999 | Green et al. |
| 6,156,359 A | | 12/2000 | Segal |
| 6,221,392 B1 | | 4/2001 | Khankari et al. |
| 6,248,363 B1 | * | 6/2001 | Patel .................. A61P 9/10 424/497 |
| 6,413,549 B2 | | 7/2002 | Green et al. |
| 6,423,342 B1 | | 7/2002 | Jordan et al. |
| 6,509,040 B1 | | 1/2003 | Murray et al. |
| 6,709,669 B1 | * | 3/2004 | Murray .............. A61K 47/42 424/434 |

FOREIGN PATENT DOCUMENTS

| | | |
|---|---|---|
| RU | 2459620 C2 | 8/2012 |
| RU | 2587717 C2 | 6/2016 |
| WO | 00/61117 A1 | 10/2000 |
| WO | 2008/119518 A1 | 10/2008 |
| WO | 2012/101500 A1 | 8/2012 |
| WO | 2012/151237 A1 | 11/2012 |

OTHER PUBLICATIONS

Foox et al. (Drug Delivery from gelatin-based systems, Expert Opinion on Drug Delivery, 12:9, 1547-1563; 2015). (Year: 2015).*

Abruzzo et al. (Chitosan/alginate complexes for vaginal delivery of chlorhexidine digluconate, Carbohydrate Polymers 91 (2013) 651-658). (Year: 2013).*

Basic Principles of Freeze Drying (SP Scientific, accessed Oct. 21, 2019). (Year: 2019).*

Vorherr et al. (Antimicrobial effect of chlorhexidine and povidone-iodine on vaginal bacteria, Journal of Infection, vol. 8, Issue 3, May 1984, pp. 195-199). (Year: 1984).*

Foox et al. (Drug Delivery from gelatin-based systems, Expert Opinion on Drug Delivery, (2015) 12:9, 1547-1563). (Year: 2015).*

Abruzzo et al. (2013). "Chitosan/alginate complexes for vaginal delivery of chlorhexidine digluconate," Carbohydrate Polymers 91 (2): 651-658.

International Search Report and Written Opinion dated Jan. 25, 2018, directed to PCT/IB2017/056373; 11 pages.

Seager, H. (1998). "Drug-delivery Products and the Zydis Fast-dissolving Dosage Form," J. Pharm. Pharmacol. (50): 375-382.

Woolfson et al. (2010). "Freeze-dried, mucoadhesive system for vaginal delivery of the HIV microbicide, dapivirine: Optimisation by an artificial neural network," International Journal of Pharmaceutics 388: 136-143.

Wu et al. (2011). "Vaginal delivery of siRNA using a novel PEGylated lipoplex-entrapped alginate scaffold system," Journal of Controlled Release 155: 418-426.

Dobaria et al. (2007). "Vaginal drug delivery systems: A Review of Current Status," East and Central African Journal of Pharmaceutical Sciences 10: 3-13.

Spencer et al. (1999). "Patient acceptability of and tolerance to a placebo intravaginal ring in hysterectomized women: a pilot study," Climacteric 2(2): 110-114.

Vermani et al. (Oct. 2000). "The scope and potential of vaginal drug delivery," PSTT 3(10): 359-364.

Office Action dated Sep. 3, 2020, directed to MX Application No. MX/a/2019/004238; 5 pages.

Examination Report dated Dec. 11, 2020, directed to IN Application No. 201927018094; 6 pages.

Borges et al. (Jan. 2015). "Drug delivery systems for vaginal infections," Frontiers in Clinical Drug Research: Anti-Infectives 2; 27 pages.

First Office Action dated Jan. 27, 2021, directed to CN Application No. 201780076778.2; 24 pages.

Office Action dated Feb. 2, 2021, directed to MX Application No. MX/a/2019/004238; 6 pages.

Official Action dated Jan. 26, 2021, directed to RU Application No. 2019113770; 12 pages.

Perioli et al. (2011). "New solid mucoadhesive systems for benzydamine vaginal administration," Colloids and Surfaces B: Biointerfaces 84; 413-420.

Pertzev et al. (1999). Pharmaceutical and Biomedical Aspects of Drugs 1; 6 pages.

Search Report dated Jan. 26, 2021, directed to RU Application No. 2019113770; 6 pages.

* cited by examiner

LYOPHILIZED PHARMACEUTICAL COMPOSITIONS FOR VAGINAL DELIVERY

REFERENCE TO RELATED APPLICATIONS

This application is a national stage application under 35 USC 371 of International Application No. PCT/IB2017/056373, filed Oct. 13, 2017, which claims priority to U.S. Provisional Application No. 62/407,709, filed Oct. 13, 2016, the entire contents of each of which are incorporated herein by reference.

FIELD OF THE INVENTION

The invention relates to a pharmaceutical dosage form suitable for vaginal delivery and method for vaginal delivery of various active ingredients. More specifically, the present invention is directed to a lyophilized pharmaceutical dosage form for vaginal delivery and methods of preparing and using the lyophilized pharmaceutical dosage form.

BACKGROUND OF THE INVENTION

Pharmaceutical formulations have been developed for vaginal delivery of therapeutic agents for the prevention, treatment and mitigation of infection or disease. Specifically, such formulations for vaginal delivery are suitable for:
  Local/topical delivery of therapeutics,
  Systemic delivery of pharmaceuticals in particular those susceptible to first pass metabolism,
  Systemic delivery of macromolecules such as proteins and peptides, and
  Mucosal delivery of vaccines.

Vaginal delivery is relatively non-invasive and by-passes first pass hepatic clearance to improve bioavailability of molecules susceptible to first pass metabolism and can also reduce the incidence and severity of gastrointestinal side effects. Also the vagina has a large permeation area with rich vascularization, which makes it a more desirable and effective location for the uptake of many active pharmaceutical ingredients.

Vaginal delivery of proteins and peptides has the advantage that it avoids the harsh environment of the gastrointestinal tract which degrades these molecules leading to poor bioavailability.

Similarly, the novel lyophilized dose formulations of the present invention having both mucoadhesive and rapid dispersion properties are ideally suited for vaginal delivery of vaccines for the treatment of infections such as HPV, HIV, *Chlamydia*, N. gonorrhoea and Hepatitis B.

The composition for vaginal delivery needs to provide a formulation that can release the active pharmaceutical ingredient (API) in the vaginal cavity. The composition must also be suitable for being handled and inserted without breakage. Preferably, the composition also dissolves or disintegrates in-vivo within a reasonable time in the vaginal cavity without generating excess discharge. Further, formulations for vaginal delivery need to avoid unduly disturbing the environment of the vaginal cavity in order to avoid inflammation or other potential complications.

Conventional vaginal delivery methods use formulations such as creams, solutions, pessaries, foams, ointments, tablets and generally prefer a short residence time at the site of administration. For vaginal delivery, short dispersion times and/or good mucoadhesion are desirable to minimize the effect of the washing action of physiological secretions of vaginal fluids. Bioadhesives, such as inserts, tablets, and gels may be used to adhere the dosage form to the vaginal mucosa to achieve sufficient contact time with the tissue. Currently, vaginal delivery methods are used for local delivery of antibacterial agents, antifungal agents, antiprotozoal agents, antiviral agents, labor-inducing agents, spermicidal agents, prostaglandins, steroids and microbicides. Some problems associated with current formulations are leakage, odor, colored discharge, irritation, itching, burning and/or swelling, as well as potential adverse effects on coitus, causing inconvenience to users sometimes leading to poor patient compliance.

Lyophilized oral formulations in the form of fast-dissolving dosage forms (FDDFs) are convenient to use and are often used to address issues of placing a tablet intra-orally so that it disperses readily and cannot be dislodged. There are many forms of FDDFs, for example, "loosely" compressed tablets comprising a large amount of wicking/disintegrating agents, tablets comprising a large amount of effervescent agents, and lyophilized tablets. Most commonly, lyophilized, FDDFs, which are designed to release the active ingredient in the oral cavity are formulated using rapidly soluble gelatin-based matrices. These dosage forms are well known and can be used to deliver a wide range of drugs. Some fast-dissolving dosage forms utilize gelatin and mannitol as carriers or matrix forming agents (Seagar, H., "Drug-Delivery Products and Zydis Fast Dissolving Dosage Form," *J. Pharm. Pharmaco*, vol. 50, p. 375-382 (1998)).

Typically, gelatin is used as a polymeric matrix forming agent and together with sugar alcohols such as mannitol imparts sufficient strength to the dosage form to prevent breakage on removal from packaging, but once placed in the mouth, the matrix allows essentially immediate dispersion of the dosage form. Hydrolyzed mammalian gelatin is often the matrix forming agent of choice in FDDFs because it gels rapidly upon cooling. A suitable hydrolyzed mammalian gelatin may be bovine gelatin. Non-gelling fish gelatin may also be used. During processing, the dosed solution/suspension is preferably frozen by passing through a gaseous medium to accomplish rapid freezing. In certain embodiments, the dosage form may comprise at least one fish gelatin and at least one bovine gelatin.

Another approach to the provision of FDDFs employs a loosely compressed tablet. To form such a tablet, the active ingredient is mixed with water-soluble diluents and compressed on a tableting machine using a low to medium compression force. This is the more conventional approach, and very often does not produce tablets with the required tensile strength and *disintegration* time. This technology may rely on the use of, super-disintegrants, effervescent agents, highly aqueous soluble excipients, and the like. The loosely compressed tablets can incorporate encapsulated pharmaceutical ingredients for taste masking or modified release, but the compression forces need to be minimized to prevent damage to the active pharmaceutical ingredient coating. See, for example, OraSolv™ technology, U.S. Pat. No. 5,178,878.

Further, rapidly dissolving tablets have been produced using suitable crystalline sugar structures under adapted curing conditions. See, for example, U.S. Pat. No. 5,866,163. Further, compressed rapidly dissolvable dosage forms including an active ingredient, a matrix composed of a non-direct compression filler, and a lubricant are disclosed in U.S. Pat. No. 6,221,392.

In one form of lyophilization, a suspension is prepared with the active ingredient and appropriate excipients. The suspension is dispensed into blister packs and freeze-dried. See, for example, U.S. Pat. No. 4,371,516. This approach usually gives tablets with porous structure of a reasonable tensile strength and disintegration time. Some similar processes are described in U.S. Pat. Nos. 4,642,903; 5,976,577; 6,156,359; 6,413,549; 6,423,342; 6,509,040; and 6,709,669.

There are a few vaginal delivery systems that are in the form of a lyophilized tablet. An article by Abruzzo, entitled, "*Chitosan/alginate complexes for vaginal delivery of chlorhexidine digluconate*", discloses a lyophilized vaginal insert. This vaginal insert is comprised of chitosan and alginate complexes and is used for local delivery of chlorhexidine digluconate for genital infections. Another article by A. David Woolf son, "*Freeze-dried, mucoadhesive system for vaginal delivery of the HIV microbidcide, dapivirine: Optimisation by an artificial neural network*, discusses a freeze-dried vaginal delivery system for delivery of an HIV microbicide. Another article by Sherry Y. Wu, "*Vaginal delivery of siRNA using a novel PEGylated lipoplex-entrapped alginate scaffold system*", relates to alginate scaffold systems containing muco-inert PEGylated lipoplexes to provide a sustained vaginal presence of lipoplexes in vivo and to facilitate the delivery of siRNA/oligonucleotides into the vaginal epithelium.

SUMMARY OF THE INVENTION

In one embodiment, there is disclosed a solid lyophilized vaginal dosage form including:
a) an effective amount of at least one active ingredient;
b) a crystalline structure forming agent in an amount of about 5 wt. % to about 40 wt. %, based on the total weight of the lyophilized dosage form; and
c) at least one polymeric mucoadhesive matrix forming agent;
wherein the dosage form has a pH of about 4.0 to 5.0, and disintegrates within 120 seconds after being contacted with a vaginal mucosa.

In some embodiments, the pharmaceutical compositions disclosed herein can be presented to vaginal mucosa as vaginal lyophilized inserts in various sizes ranges from 15 mg to 300 mg in mass. The lyophilized vaginal insert can remain intact during insertion into the vaginal cavity and may dissolves and/or disintegrate in the vaginal cavity with a reasonable residence time to allow sufficient contact time for mucosal absorption of the drug at the site of administration. In some embodiments, the solid lyophilized vaginal dosage form may disintegrate within 45 seconds of being contacted within the vaginal mucosa. In some embodiments, the solid lyophilized vaginal dosage form may disintegrate in greater than about 10 seconds to less than about 120 seconds. In some embodiments, the solid lyophilized vaginal dosage form may disintegrate within about 90 seconds, within about 10-60 seconds, or about 10-45 seconds. The disintegration time can be estimated by in-vitro assessment by wetting time test and/or low volume dispersion time test.

In each of the foregoing embodiments, the crystalline structure forming agent may be a sugar alcohol or sugar. In each of the foregoing embodiments, the crystalline structure forming agent may be selected from mannitol, xylitol, saccharose, glucose, lactose, fructose, dextrose, galactose and trehalose; as well as cyclic sugars such as cyclodextrin and combinations of two or more of the foregoing.

In each of the foregoing embodiments, the polymeric mucoadhesive matrix forming agent may include polymeric materials selected from materials derived from animal or vegetable proteins, such as bovine gelatins, non-mammalian gelatins such as fish gelatins, gelling or non-gelling gelatins, hydrolysed or non-hydrolysed gelatin, povidone, starch, modified starches including pre-gelatinised starch and hydroxypropyl starch, dextrins such as maltodextrin, HPMC (methocel), soy, wheat and psyllium seed proteins, chitosan, dextrans, polysaccharides and polypeptide/protein or polysaccharide complexes such as gelatin-acacia complexes, celluloses and modified celluloses such as, for example, methylcellulose, carboxymethyl cellulose, thiolated carboxymethyl cellulose, sodium carboxymethyl cellulose, hydroxyethyl cellulose, hydroxylpropyl methylcellulose and methylhydroxyethyl cellulose, agaros, hyaluronic acid, carrageenans, pectins, alginates including sodium alginate, polyacrylic acids, cross-linked poly(acrylic acids) such as Carbopol™ mucoadhesive polymers, polycarbophil, polyacrylates, methacrylic acid polymers, polyvinyl alcohol, polyvinyl pyrrolidone, ethylhexyacrylate, other thiolated polymers a gum selected from one or more of acacia, pectin, agar, tragacanth, guar gum, xanthan gum, locust bean gum, tara gum, karaya, gellan gum, welan gum, and rhamsan gum and any combination of two or more of the foregoing mucoadhesive matrix forming agents.

In each of the foregoing embodiments, the mucoadhesive matrix forming agent may include at least one fish gelatin. In each of the foregoing embodiments, the mucoadhesive matrix forming agent may comprise at least one bovine gelatin. In each of the foregoing embodiments, the mucoadhesive matrix forming agent may comprise at least one fish gelatin and at least one bovine gelatin.

In each of the foregoing embodiments, the dosage form may further include one or more of additional matrix forming agents which may optionally be mucoadhesive, lubricants, bulking agents, preservatives, binding agents, stabilizers, emulsifiers, solubilizers, pH modifiers, colors, fillers, and osmotic pressure regulators.

In each of the foregoing embodiments, the dosage form may comprise at least one lubricant selected from colloidal silicon dioxide, simethicone and polyoxypropylene-polyoxyethylene copolymer.

In each of the foregoing embodiments, the dosage form may comprise a pH modifier.

In each of the foregoing embodiments, the dosage form may have a porosity of at least 60%.

In each of the foregoing embodiments, the dosage form may have a physical robustness characterized by resistance to breakage during handling and insertion.

In each of the foregoing of the foregoing embodiments, the active pharmaceutical ingredient may be selected from but not limited to antinfectives, animicrobials, pre-biotics, pro-biotics, antivirals, antibiotics, antifungals, contraceptive agents, vaccine antigens and adjuvants. Some examples but not limited to include acyclovir, fluconazole, progesterone and derivatives thereof, nonoxylenol-9, terbutaline, lidocaine, testosterone and derivatives thereof, dinoprostone, *lactobacillus*, estrogen and derivatives thereof, naphthalene2-sulfonate, butoconazole, clindamycin nitrate/phosphate, neomycine sulfate, polymyxin sulfate, nystatin, clotrimazole, dextrin sulphate, glyminox, miconazole nitrate, benzalkonium chloride, sodium lauryl sulphate, tenofovir, insulin, calcitonin, danazol, acriflavine, leuprorelin acetate, metronidazole, benzydamine hydrochloride, chloramphenicol, oxybutynin, ethinyl estradiol, prostaglandins, insulin, calcitonin, vaccine antigens of HIV, HPV, *Chlamydia*, Heptatits B, gonococcus and combinations thereof.

In another embodiment, a method of delivering a therapeutic agent to a vaginal cavity is disclosed. The method comprises the step of contacting the solid lyophilized vaginal dosage form of any of the foregoing embodiments with a vaginal mucosa.

DETAILED DESCRIPTION OF THE INVENTION

Figure 1A:
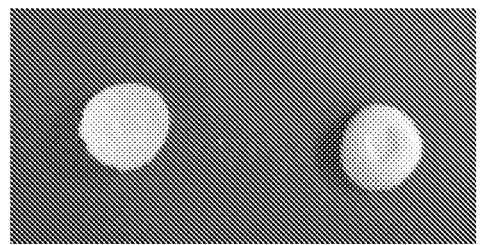
FIG. 1A illustrates a picture of the 100 mg wet dose insert of Example 1.

For illustrative purposes, the principles of the present disclosure are described by referencing various exemplary embodiments. Although certain embodiments are specifically described herein, one of ordinary skill in the art will readily recognize that the same principles are equally applicable to, and can be employed in, other devices and methods. Before explaining the disclosed embodiments of the present disclosure in detail, it is to be understood that the disclosure is not limited in its application to the details of any particular embodiment shown. Additionally, the terminology used herein is for the purpose of description and not of limitation.

The definition of a phrase or a term may include several examples. Such examples are not an exhaustive definition of the phrase or term to be defined. Such examples may also overlap with each other, may be identical to each other, and may be examples of each other.

It must be noted that as used herein and in the appended claims, the singular forms "a", "an", and "the" include plural references, unless the context clearly dictates otherwise. Furthermore, the terms "a" (or "an"), "one or more", and "at least one" can be used interchangeably herein. The terms "comprising", "including", "having", and "constructed from" can also be used interchangeably.

In one aspect, the present invention is directed to a solid lyophilized vaginal dosage form including:
  a) an effective amount of at least one active ingredient;
  b) a crystalline structure forming agent in an amount of about 5 wt. % to about 40 wt. %, based on the total weight of the lyophilized dosage form; and
  c) at least one polymeric mucoadhesive matrix forming agent;
    wherein the dosage form has a pH of about 4.0 to 5.0, and disintegrates within 120 seconds after being contacted with a vaginal mucosa.

In certain embodiments of the invention, the dosage form disintegrates within about 120, about 90, about 10-60, or about 10-45 seconds of being contacted with the vaginal mucosa. In certain embodiments of the invention, the dosage form disintegrates within 45 seconds of being contacted with the vaginal mucosa and preferably the dosage form disintegrates within 10-60, and, more preferably 10-45 seconds of being contacted with the vaginal mucosa.

The dosage form may have a porosity of at least 60% or from about 60-90%, or, more preferably, from 60% to 85%, from 60% to less than 85%, or from 60% to 75%. The porosity may be measured by techniques such as gas absorption analysis and intrusion porosimetry analysis or may be estimated from the mass of the lyophilized dosage form with respect to its wet dosing weight. The porosity of the dosage form is advantageous for providing the fast-dissolving properties. This permits the vaginal dosage form of the present invention to deliver the active ingredient in a relatively reasonable residence time in the vaginal cavity.

The dosage form the invention may have a physical robustness characterized by its resistance to breakage during handling and insertion. The physical strength of the dosage form can exhibit a tablet strength of greater than about 10N to less than 100N as measured by the Peak Load to Fracture. Due to the physical robustness of the dosage form, it may not require the use of an applicator to position the dosage form in contact with the vaginal mucosa. These properties are advantageous as they result in higher patient compliance as reduce the number of undesirable outcomes.

The dosage form may be in the form of a small disk, a sheet, a tablet, and the like. The form takes the shape of the mold or the blister pocket in which it is made or packaged. Thus, the dosage form may be circular, elliptical, square, rectangular, pentagonal, hexagonal, octagonal, and the like. The dosage form may have any of many different appearances, such as classical dish-like shapes, spherical or ellipsoid shapes, a block, a cube with rounded edges, or particular forms that may be obtainable from a suitable mold. Sizes may vary from approximately 1.5 mm diameter or a 1.5 mm dimension in the longest direction, to approximately a 20 mm diameter or longest dimension. In some embodiments, the form has a diameter of from 2 to 10 mm.

On administration, the dosage form adheres to the vaginal mucosa and rapidly takes up water from the lining of the mucosa and disintegrates within 120 seconds. The fast disintegration time allows use of a mucoadhesive solid dosage form thereby avoiding possible leakage out of the vaginal cavity that may occur with other types of dosage forms. Also, the combination of tablet physical robustness and fast dissolution avoids the need for awkward packaging, and an applicator.

The phrase "fast disintegrating dosage form", or FDDF, is a dosage form for delivering an active ingredient in a solid dosage form, which upon exposure to water, rapidly disintegrates.

The term "disintegration", the adjective form thereof, such as "disintegrating", and the verb form thereof, such as "to disintegrate", are related to the physical reaction of the dosage form in water, an aqueous solution, or fluid, such as may be found on a mucous membrane. The disintegration of the dosage form means that the structure of the dosage form breaks down from a solid, or solid-like form, to a heterogeneous mixture, a solution, a suspension, or a colloid. Because of the differences in the properties of the components of the dosage form, formation of a solution, suspension, colloid, or a heterogeneous mixture occurs after the disintegration.

An example of a disintegration test is the United States Pharmacopeia, (701) *Disintegration*, or the equivalent tests of the European Pharmacopoeia, or the Japanese Pharmacopoeia.

The dosage form will include at least one active ingredient. The active ingredient may be an active pharmaceutical ingredient, biologic or vaccine antigen for the treatment of human or veterinary diseases. The active ingredient is the component that the solid lyophilized vaginal dosage form is used to deliver. The active ingredient may be an ingredient that can be absorbed via the mucous membrane. Active ingredients may be one or more of antibacterial agents, antifungal agents, antiprotozoal agents, antiviral agents, labor-inducing agents, spermicidal agents, prostaglandins, steroids and microbicides, proteins/peptides and vaccine antigens. Preferably, the active ingredient is an active pharmaceutical ingredient.

The active pharmaceutical ingredient may be a single active pharmaceutical ingredient, such as a single chemical entity, or it may be a mixture of several active pharmaceutical ingredients. The active pharmaceutical ingredient may be of any of the many categories of active pharmaceutical ingredients. The active pharmaceutical ingredient may be selected from, but is not limited to, the group consisting of acyclovir, fluconazole, progesterone and derivatives thereof, nonoxylenol-9, terbutaline, lidocaine, testosterone and derivatives, dinoprostone, *lactobacillus*, estrogen and derivatives, naphthalene2-sulfonate, butoconazole, clindamycin nitrate/phosphate, neomycine sulfate, polymyxin sulfate, nystatin, clotrimazole, dextrin sulphate, glyminox, miconazole nitrate, benzalkonium chloride, sodium lauryl sulphate, tenofovir, insulin, calcitonin, danazol, acriflavine, leuprorelin acetate, metronidazole, benzydamine hydrochloride, chloramphenicol, oxybutynin, ethinyl estradiol, prostaglandins, insulin, calcitonin and combinations thereof. The active pharmaceutical ingredient may also be vaccine antigen such as those for the treatment of Hepatitis B, HIV, HPV, *Chlamydia*, gonococcal infections.

Active ingredients may include salts, esters, hydrates, solvates and derivatives of any of the foregoing active ingredients. Suitable derivatives are those that are known to skilled persons to possess the same activity as the active ingredient though the activity level may be lower or higher. Active ingredients may also include any active ingredient that is incompatible with oral delivery methods or compositions.

The active ingredient may be present in the lyophilized dosage form in amounts of up to 60 wt. %, or from 1-50 wt. %, or from 2-40 wt. % or from 5-25 wt. %, based on the total weight of the lyophilized dosage form.

The active ingredient may be pre-treated. Examples of pre-treated active ingredients include coated active ingredients, micro-encapsulated ingredients, nano-encapsulated ingredients, encapsulated ingredients. Such pre-treatment may be used to enhance the stability of the dosage form or may be used to modify the release profile of the active ingredient over an extended period of time.

Crystalline structure forming components are compounds which provide the required shape and tensile strength of the product. Examples of crystalline structure forming components include sugars sugar alcohols. The crystalline structure forming agent may be selected from mannitol, xylitol, saccharose, glucose, lactose, fructose, dextrose, galactose and trehalose; as well as cyclic sugars such as cyclodextrin and any combination of two or more of the foregoing. Preferred sugars and sugar alcohols are non-reducing.

The crystalline structure forming agent may be present in amounts of from 5-40 wt. %, or from 6-30 wt. %, or from 7-25 wt. % or from 8-20 wt. %, based on a total weight of the lyophilized dosage form.

Polymeric mucoadhesive matrix forming agents may include polymeric materials selected from include polymeric materials selected from materials derived from animal or vegetable proteins, such as bovine gelatins, non-mammalian gelatins such as fish gelatins, gelling or non-gelling gelatins, hydrolysed or non-hydrolysed gelatin, povidone, starch, modified starches including pre-gelatinised starch and hydroxypropyl starch, dextrins such as maltodextrin, HPMC (methocel), soy, wheat and *psyllium* seed proteins, chitosan, dextrans, polysaccharides; and polypeptide/protein or polysaccharide complexes such as gelatin-acacia complexes, celluloses and modified celluloses such as, for example, methylcellulose, carboxymethyl cellulose, thiolated carboxymethyl cellulose, sodium carboxymethyl cellulose, hydroxyethyl cellulose, hydroxylpropyl methylcellulose and methylhydroxyethyl cellulose. agaros, hyaluronic acid, carrageenans, pectins, alginates including sodium alginate, polyacrylic acids, cross-linked poly(acrylic acids) such as Carbopol™ mucoadhesive polymers, polycarbophil, polyacrylates, methacrylic acid polymers, polyvinyl alcohol, polyvinyl pyrrolidone, ethylhexyacrylate, other thiolated polymers a gum selected from one or more of acacia, pectin, agar, tragacanth, guar gum, xanthan gum, locust bean gum, tara gum, karaya, gellan gum, welan gum, and rhamsan gum and any combination of two or more of the foregoing mucoadhesive matrix forming agents.

The mucoadhesive polymeric matrix forming agent may be present in an amount of from about 1 to 60 wt. %, or from 1.5 to 55 wt. % or from 2-50 wt. %, based on a total weight of the lyophilized dosage form.

The active ingredient, crystalline structure forming component, mucoadhesive polymeric matrix former and the remaining ingredients needed to form the fast disintegrating dosage form are dissolved or suspended in an aqueous liquid. Examples of additional ingredients include additional matrix formers which may optionally be mucoadhesive, lubricants, bulking agents, preservatives, binding agents, stabilizers, emulsifiers, solubilizers, pH modifiers, colors, fillers, and osmotic pressure regulators.

Suitable anti-sticking agent/lubricant/spreading agent/wetting agent may include colloidal silicon dioxide, simethicone and polyoxypropylene-polyoxyethylene copolymers as an anti-sticking agent/lubricant/spreading agent/wetting agent.

The fast dispersing dosage form according to the invention may also contain, in addition to the active ingredient, crystalline structure forming component, and one or more mucoadhesive polymeric matrix forming agents and one or more other secondary components.

Other matrix forming agents suitable for use in the present invention include inorganic salts such as sodium phosphate, sodium chloride and aluminum silicates; and amino acids having from 2 to 12 carbon atoms such as a glycine, L-alanine, L-aspartic acid, L-glutamic acid, L-hydroxyproline, L-isoleucine, L-leucine and L-phenylalanine.

One or more matrix forming agents may be incorporated into the solution or suspension prior to solidification. The matrix forming agent may be present in addition to a surfactant or to the exclusion of a surfactant. In addition to forming the matrix, the matrix forming agent may aid in maintaining the dispersion or suspension of any active ingredient within the solution, suspension or mixture. This is especially helpful in the case of active agents that are not sufficiently soluble in water and must, therefore, be suspended rather than dissolved.

Secondary components such as preservatives, antioxidants, surfactants, viscosity enhancers, coloring agents, pH modifiers, may also be incorporated into the composition. Suitable coloring agents include red, black and yellow iron oxides and FD & C dyes such as FD & C Blue No. 2 and FD & C Red No. 40. Suitable pH modifiers include citric acid, tartaric acid, phosphoric acid, hydrochloric acid, maleic acid, sodium bicarbonate and sodium hydroxide.

The dosage form may further include one or more of excipients, other structure forming agents, flow aids, glidants, lubricants, bulking agents, preservatives, binding agents, stabilizers, emulsifiers, solubilizers, osmotic pressure regulators, buffers, and similar compounds.

The matrix is prepared by adding gelatin and mannitol in the amounts shown in Table 1, to purified water. The mixture is then heated to help the incorporation of the excipients and then cooled to ambient or sub-ambient temperature. The active ingredient and pH modifier is then added to the mix. Additional purified water may then be added to the mixture to obtain 100 parts batch size if the amount of pH modifier was unknown prior to the manufacture.

Following this step, the formulation is dosed by weight (wet dose) into the pockets of preformed blister packs. Once the solution or suspension of the active ingredient has been dosed into the pre-formed blister packs they are frozen by passage through a liquid nitrogen freeze tunnels at temperatures no warmer than −30'C. The frozen product is then lyophilized using a suitable drying temperature and vacuum. Persons skilled in the art can determine the appropriate lyophilization conditions suitable for a particular formulation.

The resulting lyophilized inserts have a very high porosity of at least 60%, which allows rapid disintegration. The blister packs containing the lyophilized inserts are then sealed with a lidding foil.

In general terms, a suitable solid lyophilized vaginal dosage form of the present invention may include one or more of the components in the ranges listed in the following table.

TABLE 1

| Component | Wt. % (Prior to Lyophilization) | Wt % (After Lyophilization) |
| --- | --- | --- |
| Fish Gelatin | 0-10 | 0-60 |
| Bovine Gelatin | 0-10 | 0-60 |
| Maltodextrin | 0-10 | 0-50 |
| HP Starch | 0-10 | 0-50 |
| Active Ingredient | 0.1-10 | 1-60 |
| Crystalline structure forming | 1-8 | 5-40 |
| Colloidal silicon dioxide | 0-2 | 0-10 |
| Simethicone | 0-2 | 0-10 |
| Polyoxypropylene-polyoxyethylene | 0-0.3 | 0-1.5 |
| Hydroxypropyl | 0-2 | 0-10 |
| Hydroxyethylcellulose | 0-1 | 0-5 |
| Chitosan | 0-2 | 0-10 |
| Water | 60-90 | Removed by lyophilization |
| Total | 100 | 100 |

The percentages of each component above represent the weight percent of each component, based upon the total weight of the final solid lyophilized vaginal dosage form.

Table 2 below shows the range in mg of pharmaceutical composition present per tablet present in examples of three wet dosing weights of the liquid formulation prior to lyophilization.

TABLE 2

| | Range mg/insert (Finished Product) | | |
| --- | --- | --- | --- |
| Components | Wet dose: 100 mg | Wet dose: 500 mg | Wet dose: 1000 mg |
| Fish Gelatin | 1 to 10 | 5 to 50 | 10 to 100 |
| Bovine Gelatin | 1 to 10 | 5 to 50 | 10 to 100 |
| Maltodextrin | 0 to 10 | 0 to 50 | 0 to 100 |

TABLE 2-continued

| Components | Range mg/insert (Finished Product) | | |
|---|---|---|---|
| | Wet dose: 100 mg | Wet dose: 500 mg | Wet dose: 1000 mg |
| HP Starch | 0 to 10 | 0 to 50 | 0 to 100 |
| Acyclovir - Active Pharmaceutical Ingredient | 10 | 0.5 to 50 | 100 |
| Mannitol | 1 to 8 | 0.5 to 40 | 10 to 80 |
| pH modifier (pH required: pH 4.5 ± 0.5) | No claim - range is pH dependent | | |
| Colloidal Silicon Dioxide | 0 to 2 | 0 to 8 | 0 to 20 |
| Simethicone | 0 to 2 | 0 to 10 | 0 to 20 |
| polyoxypropylene polyoxyethylene copolymer e.g. poloxomer 188 | (0.033 - no claim) | (0.175 - no claim) | (0.33 - no claim) |
| Hydroxypropylmethylcellulose (HPMC) | 0 to 2 | 0 to 10 | 0 to 20 |
| Hydroxyethyl cellulose (HEC) | 0 to 1 | 0 to 5 | 0 to 10 |
| Chitosan | 0 to 2 | 0 to 10 | 0 to 20 |
| Purified water Qs 100% batch size, sublimed during freeze drying | 60-90 | 300-450 | 600-900 |

The invention also relates to a method for vaginal delivery of an active ingredient including the step of inserting a dosage form as described above into the vaginal cavity. The vaginal route of administration offers many advantages in comparison with the oral route. For example, the vaginal route can be used to avoid first pass metabolism of the active ingredient which may occur as a result of oral administration, e.g. in the digestive tract. Also, the vaginal administration route can result in a reduction in the incidence and severity of gastrointestinal side effects. Also, the vaginal delivery method takes advantage of the large permeation area and rich vascularization of the vagina.

An important advantage of the present invention results from the combination of the physical robustness of the dosage form and its ability to dissolve in 120 seconds or less. This enables self-insertion of the dosage form often without the need for special packaging or a special applicator. This is an important advantage since it typically leads to a significant improvement in patient compliance by making the product easy to use. The vaginal dosage form of the invention may also be fabricated to be odorless and/or colorless. It avoids the problems of leakage out of the vaginal cavity, messiness or feeling of fullness and the dosage form typically avoids irritation, itching, burning or swelling. Finally, the dosage form can be fabricated to have no adverse effect on coitus and can be applied at an appropriate time in accordance to treatment requirements prior to intercourse.

Lyophilized pharmaceutical compositions for vaginal delivery can provide a convenient dosage form that can be administered by the patients without the need of an applicator. Lyophilized inserts are robust and thus can be applied in the vagina without breaking. Upon administration, the inserts will start to disintegrate and the active pharmaceutical ingredient will start to dissolve in the vaginal cavity. The compositions for the lyophilized vaginal inserts may contain one or more components which possess mucoadhesive properties preventing leakage out of the vaginal cavity.

The following examples are illustrative, but not limiting, of the methods and compositions of the present disclosure. Other suitable modifications and adaptations of the variety of conditions and parameters normally encountered in the field, and which are obvious to those skilled in the art, are within the spirit and the scope of the disclosure. All patents and publications cited herein are fully incorporated by reference herein in their entirety.

Examples 1 and 2 are typical reference compositions of lyophilized tablets which can be used for oral delivery. Examples 3-12 are formulation compositions proposed under the lyophilized vaginal inserts described herein.

EXAMPLES

Example 1—Bovine Gelatin (Reference Composition)

The process for preparing the pharmaceutical composition and the lyophilized tablets is described below:

Mixing Process:

The matrix of the finished product is prepared by adding gelatin and mannitol to the purified water. The mixture is then heated to 60° C. to help the incorporation of the excipients and then cooled to ambient temperature (23° C.). The active pharmaceutical ingredient and pH modifier is then added to the mix. Additional purified water may then be added to the mix to obtain 100% batch size if the amount of pH modifier was unknown prior to the manufacture.

Bovine gelatin was used in this pharmaceutical composition. Acyclovir was used as a model drug.

Dosing, Freezing and Freeze-Drying Process:

The formulation is dosed by weight (wet dose) into the pockets of preformed blister packs. Once dosed, the blister packs are passed through a liquid nitrogen freezing tunnel where the water in the mixture is frozen within the blister pockets. On exiting the freeze tunnel, the product is stored frozen in refrigerated cabinets prior to freeze-drying. The frozen inserts are then loaded onto the shelves of a freeze-dryer where the ice crystals are removed from the inserts by sublimation at low pressure. The resulting lyophilized inserts have a very high porosity of typically at least 60%, which allows for rapid disintegration.

In each of the tables of the examples, the "wet dose" refers to the material prior to lyophilization.

Figure 1B:
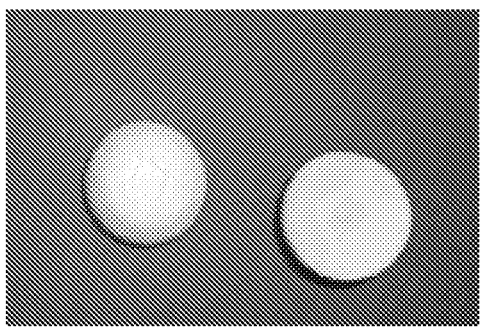
FIG. 1B illustrates a picture of the 500 mg wet dose insert of Example 1.
Figure 1C:
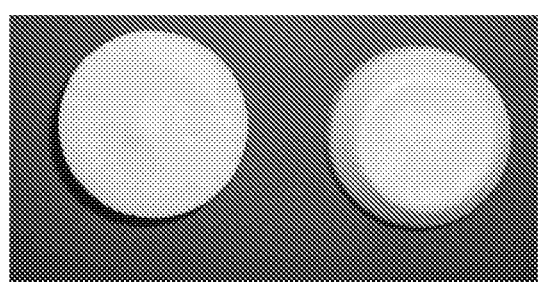
FIG. 1C illustrates a picture of the 1000 mg wet dose insert of Example 1.

| Composition 1 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Bovine Gelatin | 4.00 | 23.50 | 4.00 | 20.00 | 40.00 |
| Mannitol | 3.00 | 17.60 | 3.00 | 15.00 | 30.00 |
| Acyclovir | 10.00 | 58.80 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 17.00 | 85.00 | 170.00 |
| Appearance: Good - A robust lyophilized tablet, free of defects that can be removed from the packaging and handled without breaking | | | FIG. 1A | FIG. 1B | FIG. 1C |
| % Porosity | | | | 83% | |
| Wetting Time | | | <2 seconds | <7 seconds | <12 seconds |
| Low Volume Dispersion Time | | | <2 seconds | <2 seconds | <7 seconds |
| Tablet Peak Load to Fracture | | | Data not generated | Data not generated | 15.4N |

Example 2—Fish Gelatin (Reference Composition)

The process of Example 1 as described above was repeated for the below components except that fish gelatin was used instead of bovine. The amounts of fish gelatin and mannitol were adjusted as indicated below

Figure 2A:
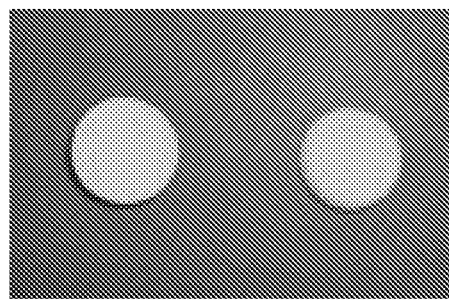
FIG. 2A illustrates a picture of the 100 mg wet dose insert of Example 2.
Figure 2B:
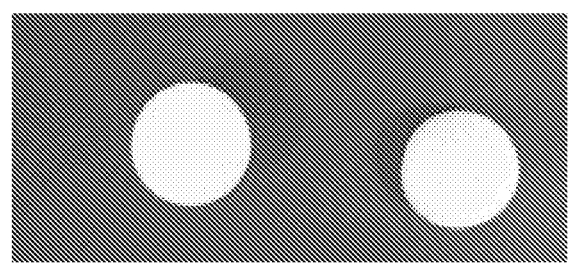
FIG. 2B illustrates a picture of the 500 mg wet dose insert of Example 2.
Figure 2C:
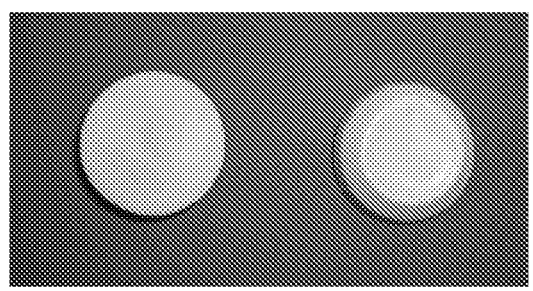
FIG. 2C illustrates a picture of the 1000 mg wet dose insert of Example 2.

| Composition 2 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Fish Gelatin | 5.00 | 26.70 | 5.00 | 25.00 | 50.00 |
| Mannitol | 3.75 | 20.00 | 3.75 | 18.75 | 37.50 |
| Acyclovir | 10.00 | 53.30 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 18.75 | 93.75 | 187.50 |
| Appearance: Good - A robust lyophilized tablet, free of defects that can be removed from the packaging and handled without breaking | | | FIG. 2A | FIG. 2B | FIG. 2C |
| % Porosity | | | | 81.25% | |
| Wetting Time | | | <1 seconds | <2 seconds | <2 seconds |
| Low Volume Dispersion Time | | | <2 seconds | <2 seconds | <4 seconds |
| Tablet Peak Load to Fracture | | | Data not generated | Data not generated | 13.3N |

Example 3—Fish Gelatin (Composition for Vaginal Insert)

The process of Example 2 as described above was repeated for Example 3 except that the amounts of fish gelatin and mannitol were increased as indicated below.

| Composition 3 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Fish Gelatin | 8.00 | 33.00 | 8.00 | 40.00 | 80.00 |
| Mannitol | 6.00 | 25.00 | 6.00 | 30.00 | 60.00 |
| Acyclovir | 10.00 | 42.00 | 10.00 | 50.00 | 100.00 |

Figure 3A:
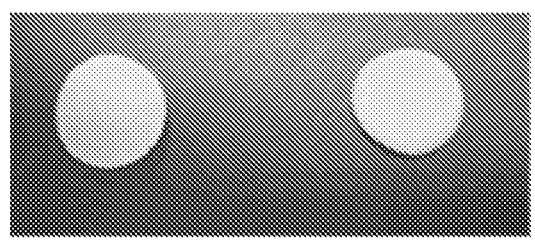
FIG. 3A illustrates a picture of the 100 mg wet dose insert of Example 3.
Figure 3B:
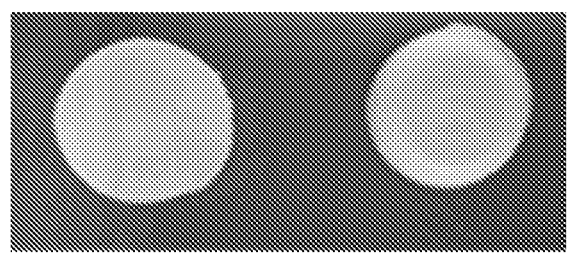
FIG. 3B illustrates a picture of the 500 mg wet dose insert of Example 3.
Figure 3C:
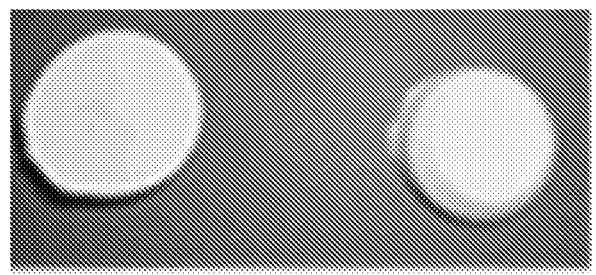
FIG. 3C illustrates a picture of the 1000 mg wet dose insert of Example 3.

| Composition 3 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 24.00 | 120.00 | 240.00 |
| Appearance: Good - A robust lyophilized tablet, free of defects that can be removed from the packaging and handled without breaking | | | FIG. 3A | FIG. 3B | FIG. 3C |
| % Porosity | | | | 76% | |
| Wetting Time | | | <1 second | <2 seconds | <5 seconds) |
| Low Volume Dispersion Time | | | <2 seconds | <2 seconds | <6 seconds |
| Tablet Peak Load to Fracture | | | Data not generated | Data not generated | 33.6N |

Example 4—Fish Gelatin Plus HPMC (Composition for Vaginal Insert)

The process of Example 3 as described above was repeated for the below components in the indicated amounts except for the addition of hydroxypropyl methylcellulose (Methocel E15LV)) in the formulation. Hydroxypropyl methylcellulose is manually blended with the mannitol to facilitate its incorporation. Homogenization was required prior to the pH adjustment to ensure the mixture is homogeneous.

Figure 4A:
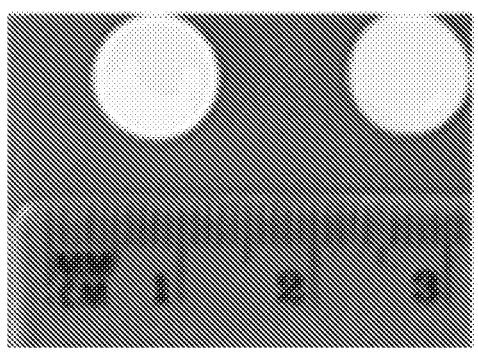
FIG. 4A illustrates a picture of the 100 mg wet dose insert of Example 4.
Figure 4B:
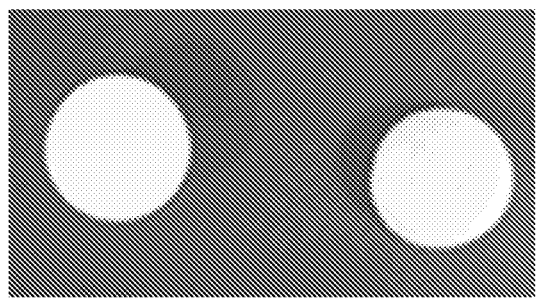
FIG. 4B illustrates a picture of the 500 mg wet dose insert of Example 4.

| Composition 4 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Fish Gelatin | 8.00 | 30.77 | 8.00 | 40.00 | 80.00 |
| Mannitol | 6.00 | 23.08 | 6.00 | 30.00 | 60.00 |
| Hydroxypropyl methylcellulose | 2.00 | 7.69 | 2.00 | 10.00 | 20.00 |
| Acyclovir | 10.00 | 38.46 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 26.00 | 130.00 | 260.00 |
| Appearance: Good - A robust, lyophilized tablet, free of defects that can be removed from the packaging and handled without breaking | | | FIG. 4A | FIG. 4B | Data not generated |
| % Porosity | | | | 74% | |
| Wetting Time | | | <9 seconds | <36 seconds | Data not generated |
| Low Volume Dispersion Time | | | <15 seconds | >60 seconds and <120 seconds | Data not generated |
| Tablet Peak Load to Fracture | | | Data not generated | 73.5N | Data not generated |

Example 5—Fish Gelatin Plus Colloidal Silicon Dioxide (Composition for Vaginal Insert)

The process of Example 3 as described above was repeated for the below components in the indicated amounts except for the addition of colloidal silicon dioxide in the composition.

Figure 5A:
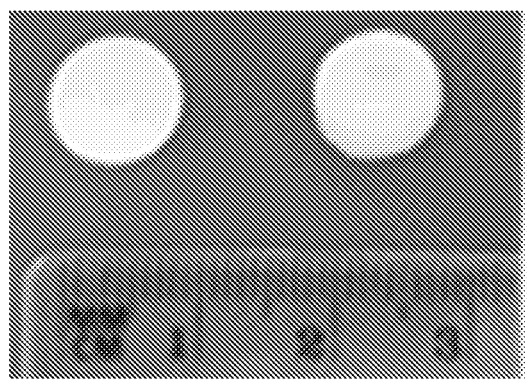
FIG. 5A illustrates a picture of the 100 mg wet dose insert of Example 5.
Figure 5B:
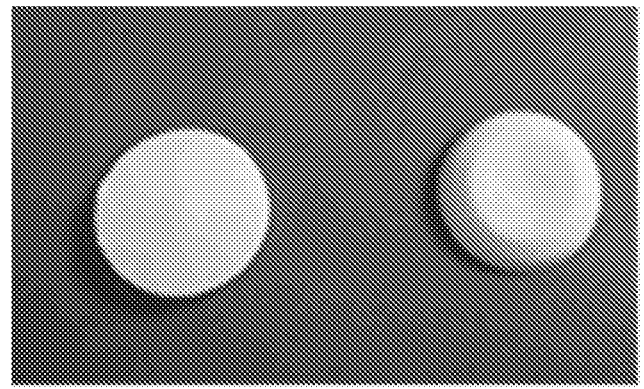
FIG. 5B illustrates a picture of the 500 mg wet dose insert of Example 5.

| Composition 5 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Fish Gelatin | 8.00 | 31.37 | 8.00 | 40.00 | 80.00 |
| Mannitol | 6.00 | 23.53 | 6.00 | 30.00 | 60.00 |
| Colloidal Silicon Dioxide | 1.50 | 5.88 | 1.50 | 7.50 | 15.00 |
| Acyclovir | 10.00 | 39.22 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 25.50 | 127.50 | 255.00 |
| Appearance: Good - A robust, lyophilized tablet, free of defects that can be removed from the packaging and handled without breaking | | | FIG. 5A | FIG. 5B | Data not generated |
| % Porosity | | | | 74.5% | |
| Wetting Time | | | <6 seconds | <22 seconds | Data not generated |
| Low Volume Dispersion Time | | | <17 seconds | >60 seconds and <120 seconds | Data not generated |
| Tablet Peak Load to Fracture | | | Data not generated | 55.6N | Data not generated |

Example 6—Fish Gelatin Plus Simethicone and Polyoxypropylene-Polyoxyethylene Copolymer (Composition for Vaginal Insert)

The process of Example 3 as described above was repeated for the below components in the indicated amounts except for the addition of simethicone and polyoxypropylene-polyoxyethylene copolymer (poloxamer 188) which were incorporated in this order and prior to pH adjustment.

Figure 6:
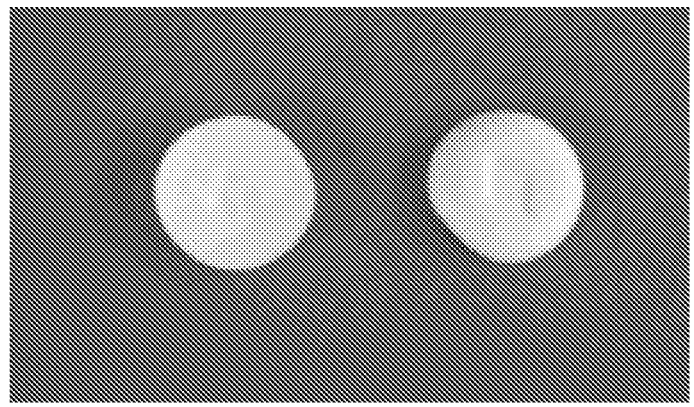
FIG. 6 illustrates a picture of the 100 mg wet dose insert of Example 6.

| Composition 6 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Fish Gelatin | 8.00 | 30.73 | 8.00 | 40.00 | 80.00 |
| Mannitol | 6.00 | 23.05 | 6.00 | 30.00 | 60.00 |
| Simethicone | 2.00 | 7.68 | 2.00 | 10.99 | 20.00 |
| polyoxypropylene-polyoxyethylene copolymer | 0.033 | 0.13 | 0.033 | 0.165 | 0.33 |
| Acyclovir | 10.00 | 38.41 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 26.033 | 130.16 | 260.33 |
| Appearance: Good - A robust, lyophilized tablet, free of defects that can be removed from the packaging and handled without breaking | | | FIG. 6 | Data not generated | Data not generated |
| % Porosity | | | | 74% | |
| Wetting Time | | | <9 seconds | Data not generated | Data not generated |
| Low Volume Dispersion Time | | | <31 seconds | Data not generated | Data not generated |
| Tablet Peak Load to Fracture | | | 48.3N | Data not generated | Data not generated |

Example 7—Fish Gelatin Plus Hydroxyethyl Cellulose (Composition for Vaginal Insert)

The process of Example 3 as described above was repeated for the below components in the indicated amounts except for the addition of hydroxyethyl cellulose in the composition. HEC was added prior to the API addition.

Figure 7A:
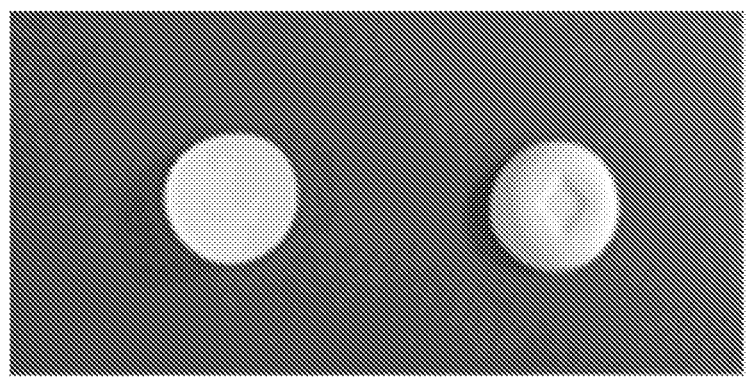
FIG. 7A illustrates a picture of the 100 mg wet dose insert of Example 7.
Figure 7B:
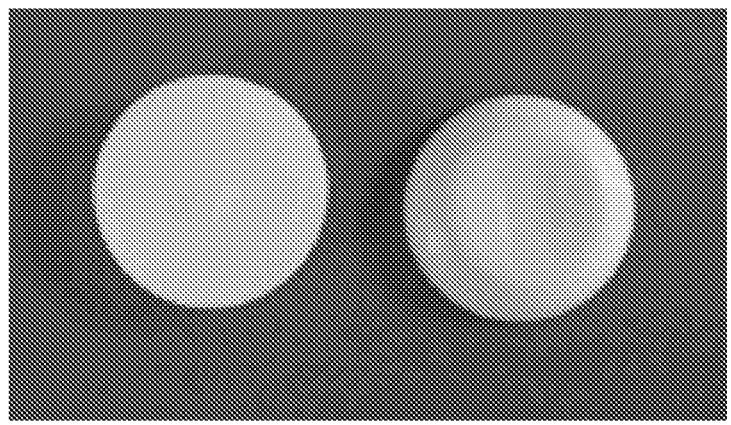
FIG. 7B illustrates a picture of the 500 mg wet dose insert of Example 7.

| Composition 7 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Fish Gelatin | 8.00 | 32.65 | 8.00 | 40.00 | 80.00 |
| Mannitol | 6.00 | 24.49 | 6.00 | 30.00 | 60.00 |
| Hydroxyethyl cellulose | 0.50 | 2.04 | 0.50 | 2.50 | 5.00 |
| Acyclovir | 10.00 | 40.82 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 24.50 | 122.50 | 245.00 |
| Appearance: Good - A robust, lyophilized tablet, free of defects that can be removed from the packaging and handled without breaking | | | FIG. 7A | FIG. 7B | Data not generated |
| % Porosity | | | | 75.5% | |
| Wetting Time | | | <6 seconds | >60 seconds and <120 seconds | Data not generated |
| Low Volume Dispersion Time | | | <7 seconds | >60 seconds and <120 seconds | Data not generated |
| Tablet Peak Load to Fracture | | | Data not generated | 48.8 N | Data not generated |

Example 8—Fish Gelatin Plus Hydroxyethyl Cellulose (Composition for Vaginal Insert)

The process of Example 3 as described above was repeated for the below components in the indicated amounts except for the addition of chitosan in the composition. Chitosan was added prior to the API addition.

Figure 8:
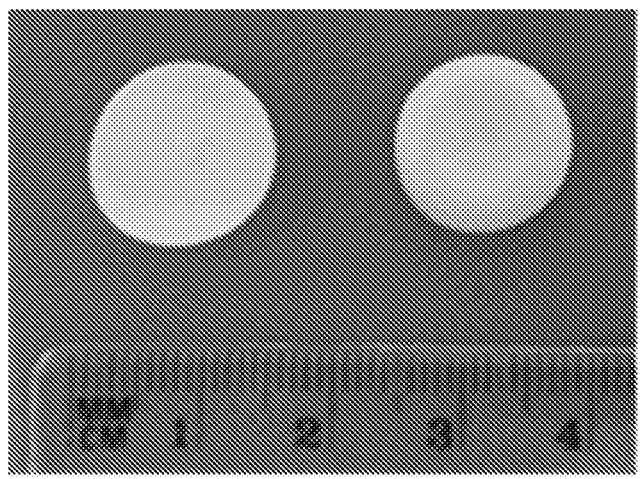
FIG. 8 illustrates a picture of the 500 mg wet dose insert of Example 8.

| Composition 8 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Fish Gelatin | 8.00 | 32.00 | 8.00 | 40.00 | 80.00 |
| Mannitol | 6.00 | 24.00 | 6.00 | 30.00 | 60.00 |
| Chitosan | 1.00 | 4.00 | 1.00 | 5.00 | 10.00 |
| Acyclovir | 10.00 | 40.00 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 25.00 | 125.00 | 250.00 |
| Appearance: Good - A robust, lyophilized tablet, free of defects that can be removed from the packaging and handled without breaking | | | No photograph taken | FIG. 8 | Data not generated |
| % Porosity | | | | 75% | |
| Wetting Time | | | <8 seconds | >60 seconds and <120 seconds | Data not generated |
| Low Volume Dispersion Time | | | <13 seconds | >60 seconds and <120 seconds | No data generated |
| Tablet Peak Load to Fracture | | | Data not generated | -45.8 N | Data not generated |

Example 9—Bovine Gelatin (Composition for Vaginal Insert)

The process of Example 1 as described above was repeated for the below components in the indicated amounts except that the amounts of bovine gelatin and mannitol were increased as indicated below.

Figure 9A:
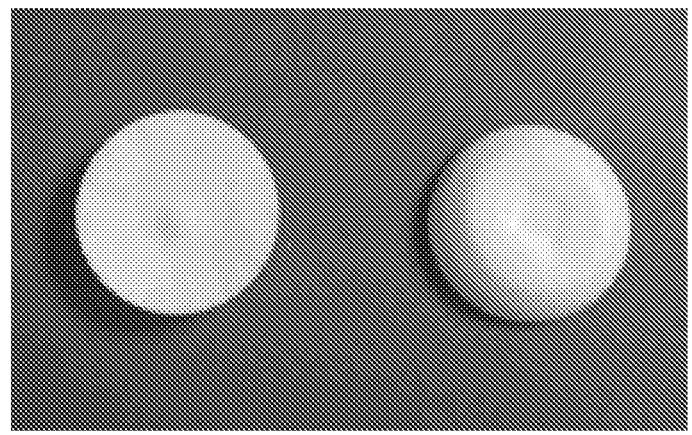
FIG. 9A illustrates a picture of the 500 mg wet dose insert of Example 9.
Figure 9B:
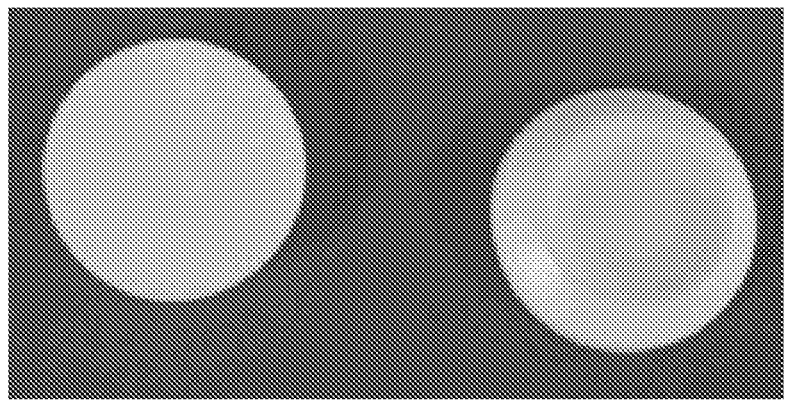
FIG. 9B illustrates a picture of the 1000 mg wet dose insert of Example 9.

| Composition 9 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Bovine Gelatin | 6.00 | 30.00 | 6.00 | 30.00 | 60.00 |
| Mannitol | 4.00 | 20.00 | 4.00 | 20.00 | 40.00 |
| Acyclovir | 10.00 | 50.00 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 20.00 | 100.00 | 200.00 |
| Appearance: Good - A robust, lyophilized tablet, free of defects that can be removed from the packaging and handled without breaking | | | No photograph taken | FIG. 9A | FIG. 9B |
| % Porosity | | | | 80% | |
| Wetting Time | | | <7 seconds | >60 seconds and <120 seconds | <35 seconds |
| Low Volume Dispersion Time | | | <3 seconds | <38 seconds and <120 seconds | >60 seconds and <120 seconds |
| Tablet Peak Load to Fracture | | | Data not generated | Data not generated | 28.9 N |

Maltodextrin

Example 10—Fish Gelatin and Maltodextrin (Composition for Vaginal Insert)

The process of Example 3 as described above was repeated for the below components in the indicated amounts except for the addition of maltodextrin which was incorporated at the same time as gelatin and mannitol in the process. In addition, the amounts of fish gelatin and mannitol were reduced.

Figure 10A:
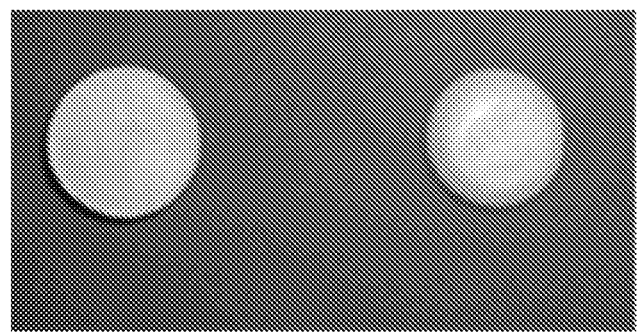
FIG. 10A illustrates a picture of the 500 mg wet dose insert of Example 10.
Figure 10B:
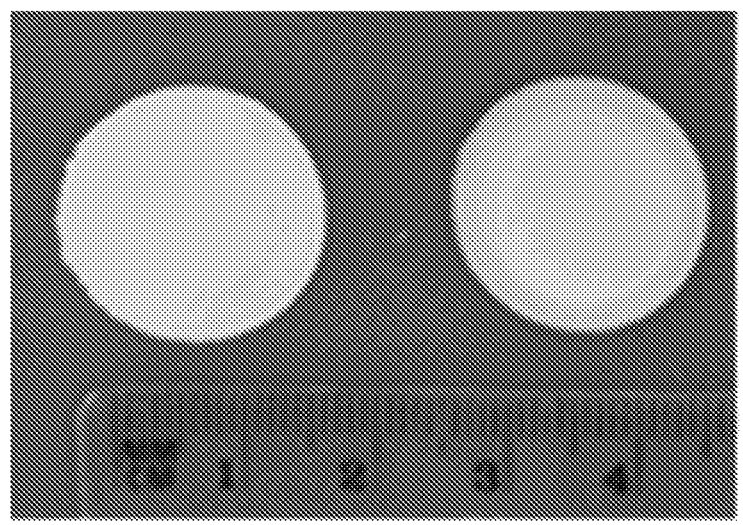
FIG. 10B illustrates a picture of the 1000 mg wet dose insert of Example 10.

| Composition 10 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| Maltodextrin | 9.00 | 37.50 | 9.00 | 45.00 | 90.00 |
| Fish Gelatin | 2.00 | 8.33 | 2.00 | 10.00 | 20.00 |
| Mannitol | 3.00 | 12.50 | 3.00 | 15.00 | 30.00 |
| Acyclovir | 10.00 | 41.67 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 24.00 | 120.00 | 240.00 |
| Appearance: Good - A robust, lyophilized tablet, free of defects that can be removed from the packaging and handled without breaking | | | Data not generated | FIG. 10A | FIG. 10B |
| % Porosity | | | | 76% | |
| Wetting Time | | | Data not generated | <3 seconds | >60 seconds and <120 seconds |
| Low Volume Dispersion Time | | | Data not generated | >60 seconds and <120 seconds | >60 seconds and <120 seconds |
| Tablet Peak Load to Fracture | | | Data not generated | Data not generated | 9.7 N |

Hydroxypropyl Starch (HP Starch)

Example 11—HP Starch with Fish Gelatin (Composition for Vaginal Insert)

The process of Example 1 as described above was repeated for the below components in the indicated amounts except for the addition of HP starch which was incorporated at the same time as fish gelatin and mannitol in the process. The amounts of fish gelatin and mannitol are reduced.

Figure 11A:
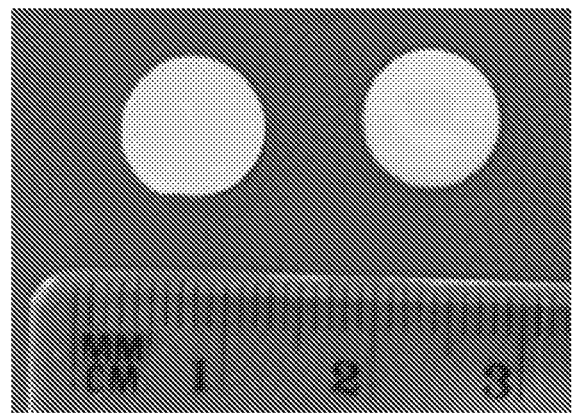
FIG. 11A illustrates a picture of the 100 mg wet dose insert of Example 11.
Figure 11B:
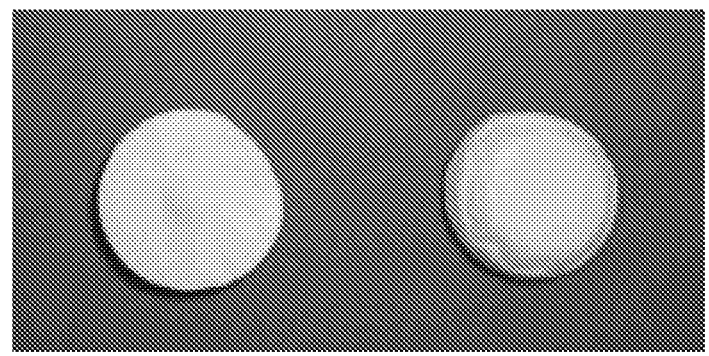
FIG. 11B illustrates a picture of the 500 mg wet dose insert of Example 11.
Figure 11C:
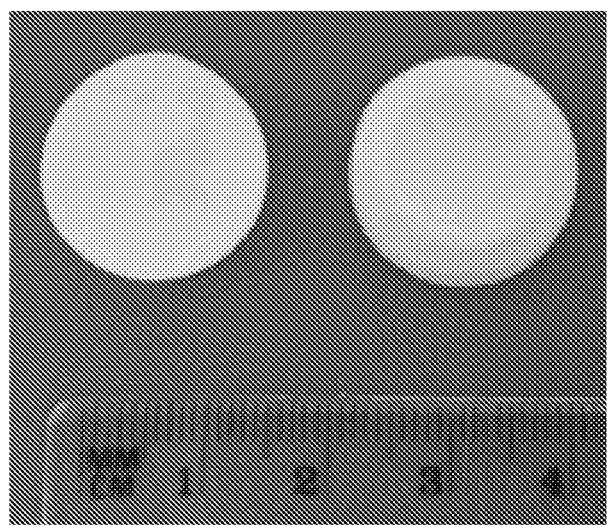
FIG. 11C illustrates a picture of the 1000 mg wet dose insert of Example 11.

| Composition 11 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| HP Starch | 9.00 | 40.91 | 9.00 | 45.00 | 90.00 |
| Fish Gelatin | 1.00 | 4.55 | 1.00 | 5.00 | 10.00 |
| Mannitol | 2.00 | 9.00 | 2.00 | 10.00 | 20.00 |
| Acyclovir | 10.00 | 45.45 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 22.00 | 110.00 | 220.00 |
| Appearance: Good - A robust, lyophilized tablet, free of defects that can be removed from the packaging and handled without breaking | | | FIG. 11A | FIG. 11B | FIG. 11C |
| % Porosity | | | | 78% | |
| Wetting Time | | | >60 seconds and <120 seconds | >60 seconds and <120 seconds | >60 seconds and <120 seconds |
| Low Volume Dispersion Time | | | >60 seconds and <120 seconds | >60 seconds and <120 seconds | >60 seconds and <120 seconds |
| Tablet Peak Load to Fracture | | | Data not generated | Data not generated | 12.1 N |

Example 12—HP Starch with Bovine Gelatin (Composition for Vaginal Insert)

The process of Example 3 as described above was repeated for the below components in the indicated amounts except for the addition of HP starch which was incorporated at the same time as bovine gelatin and mannitol in the process. The amounts of bovine gelatin and mannitol are reduced.

Figure 12A:
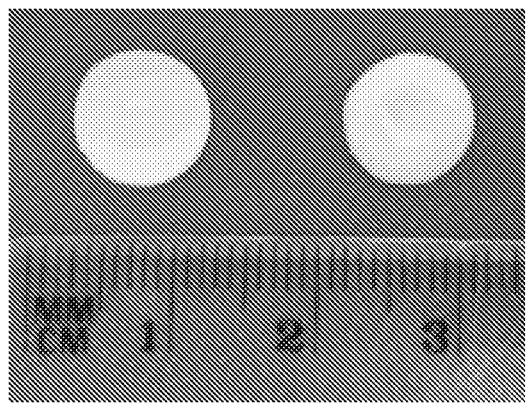
FIG. 12A illustrates a picture of the 100 mg wet dose insert of Example 12.
Figure 12B:
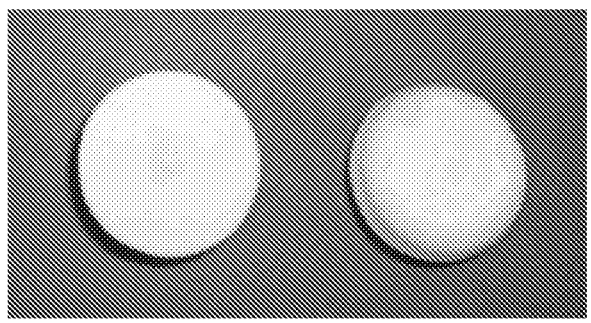
FIG. 12B illustrates a picture of the 500 mg wet dose insert of Example 12.
Figure 12C:
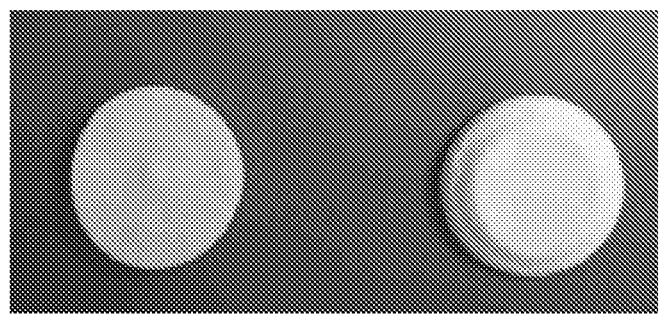
FIG. 12C illustrates a picture of the 1000 mg wet dose insert of Example 12.

| Composition 12 | % composition Before lyophilization | % composition After lyophilization | (mg/insert) Wet dose: 100 mg | (mg/insert) Wet dose: 500 mg | (mg/insert) Wet dose: 1000 mg |
|---|---|---|---|---|---|
| HP Starch | 9.00 | 40.91 | 9.00 | 45.00 | 90.00 |
| Bovine Gelatin | 1.00 | 4.55 | 1.00 | 5.00 | 10.00 |
| Mannitol | 2.00 | 9.00 | 2.00 | 10.00 | 20.00 |
| Acyclovir | 10.00 | 45.45 | 10.00 | 50.00 | 100.00 |
| pH modifier | Qs pH 4.5 | Negligible | Qs pH 4.5 (±0.5) | Qs pH 4.5 (±0.5) | Qs pH 4.5 (±0.5) |
| Purified Water | Qs to 100% batch size | Removed during lyophilization | Qs 100% batch size | Qs 100% batch size | Qs 100% batch size |
| Total Tablet Weight | N/A | 100 | 22.00 | 110.00 | 220.00 |
| Appearance: Good - A robust, lyophilized tablet, free of defects that can be removed from the packaging and handled without breaking | | | FIG. 12A | FIG. 12B | FIG. 12C |
| % Porosity | | | | 78% | |
| Wetting Time | | | >60 seconds and <120 seconds | >60 seconds and <120 seconds | >60 seconds and <120 seconds |
| Low Volume Dispersion Time | | | <9 seconds | <13 seconds | >60 seconds and <120 seconds |
| Tablet Peak Load to Fracture | | | Data not generated | Data not generated | 13.6 N |

The foregoing examples have been presented for the purpose of illustration and description only and are not to be construed as limiting the scope of the invention in any way. The scope of the invention is to be determined from the claims appended hereto.

Tests

Wetting Time Assessment Test:

The wetting time assessment test is an in-process test. The wetting time is defined as the time required for the unit to be visually wetted. It is measured for a minimum of three Zydis® units in purified water at 20° C.±0.5° C. This test was performed in approximately 200 ml of water in a beaker.

Low Volume Dispersion Time Assessment:

The low volume dispersion time assessment test is an in-process test. The time is defined as the time required for the tablet to visually show the $1^{st}$ signs of dissolution or break up of the thickest part of the tablet. It is measured for a minimum of three Zydis® units in a buffer solution of pH 4.5±0.5 at 37° C.±2° C. This test was performed in 5 ml of the buffer solution in a watchglass.

Tablet Breaking Strength (Peak Load to Fracture):

Tablet robustness is assessed by the breaking strength of the tablet as measured by the peak load required to fracture or snap the tablet. The test is performed with a three-point bending fixture with a 6 mm gap between the support. The tablet is supported at either end and deformed in its center with a knife-like probe, causing it to fracture and break at its weakest point. The test speed was 0.05 minis and the test was stopped when a break was detected. The peak load to fracture indicates the breaking strength of the tablet. The more robust tablets will give a higher peak load to fracture. This information can be used to gauge the tablet's resistance to damage that might occur during insertion of the vaginal inserts into the vaginal cavity.

Vaginal Insert Porosity:

The porosity of the vaginal insert is a theoretical estimation based on weight of the lyophilized tablet/insert and the wet dose weight prior to lyophilization. For each lyophilized tablet/insert, an aliquot of the pharmaceutical composition is metered into a pre-form pocket on a blister. The dimension and shape of the insert is determined by the geometry of the blister pocket. The porous nature of lyophilized insert is formed by the removal of the water as ice crystals by sublimation. As the dimension and shape of the insert is maintained prior to and post lyophlization, the % porosity can be estimate by as follows: % porosity=(dry weight of lyophilized tablet/Wet dose weight)×100

All documents cited herein are hereby incorporated by reference in their entirety.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein. Finally, the entire disclosure of the patents and publications referred in this application are hereby incorporated herein by reference.

What is claimed:

1. A solid lyophilized vaginal dosage form including:
   a) an effective amount of at least one active ingredient;
   b) a crystalline structure forming agent in an amount of 12.5 wt. % to 25 wt. %, based on the total weight of the lyophilized dosage form; and
   c) at least one polymeric mucoadhesive matrix forming agent;
   wherein the dosage form disintegrates within 120 seconds after being contacted with a vaginal mucosa.

2. The solid lyophilized vaginal dosage form of claim 1, wherein the dosage form disintegrates within 90 seconds of being contacted with the vaginal mucosa.

3. The solid lyophilized vaginal dosage form of claim 1, wherein the mucoadhesive matrix forming agent comprises at least one fish gelatin.

4. The solid lyophilized vaginal dosage form of claim 1, wherein the mucoadhesive matrix forming agent comprises at least one bovine gelatin.

5. The solid lyophilized vaginal dosage form of claim 1, wherein the mucoadhesive matrix forming agent comprises 1 to 60 wt. % based on the total weight of the lyophilized dosage form.

6. The solid lyophilized vaginal dosage form of claim 1, wherein the crystalline structure forming agent comprises a sugar or sugar alcohol.

7. The solid lyophilized vaginal dosage form of claim 1, wherein the crystalline structure forming agent comprises a structure forming agent selected from mannitol, xylitol, saccharose, glucose, lactose, fructose, dextrose, galactose, trehalose, cyclodextrin and any combination thereof.

8. The solid lyophilized vaginal dosage form of claim 1, wherein the dosage form further comprises at least one lubricant selected from colloidal silicon dioxide, simethicone, and polyoxypropylene-polyoxyethylene copolymer.

9. The solid lyophilized vaginal dosage form of claim 1, wherein the dosage form comprises a mucoadhesive matrix forming agent selected from chitosan, methylcellulose and hydroxyethylcellulose and hydroxypropyl methylcellulose polymers.

10. The solid lyophilized vaginal dosage form of claim 1, wherein the dosage form comprises a mucoadhesive matrix forming agent selected from gelling or non-gelling gelatins, hydrolysed or non-hydrolysed gelatin, povidone, starch, modified starches, dextrins, soy, wheat and *psyllium* seed proteins, chitosan, dextrans, polysaccharides, polypeptide/protein or polysaccharide complexes, gelatin-acacia complexes, methylcellulose, carboxymethyl cellulose, thiolated carboxymethyl cellulose, sodium carboxymethyl cellulose, hydroxyethyl cellulose, hydroxylpropyl methylcellulose and methylhydroxyethyl cellulose, agaros, hyaluronic acid, carrageenans, pectins, alginates, polyacrylic acids, cross-linked poly(acrylic acids), polycarbophil, polyacrylates, methacrylic acid polymers, polyvinyl alcohol, polyvinyl pyrrolidone, ethylhexyacrylate, other thiolated polymers, gums and any combination thereof.

11. The solid lyophilized vaginal dosage form of claim 1, wherein the dosage form further comprises a pH modifier.

12. The solid lyophilized vaginal dosage form of claim 1, wherein the dosage form has a porosity of at least 60%.

13. The solid lyophilized vaginal dosage form of claim 1, wherein the dosage form has a porosity of from 60% to under 85%.

14. The solid lyophilized vaginal dosage form of claim 1, wherein the dosage form has a physical robustness sufficient to resist breakage with handling and insertion of the dosage form into the vaginal cavity.

15. The solid lyophilized vaginal dosage form of claim 1, wherein the dosage form has a tablet strength greater than 10N to less than 100N as measured by the Peak Load to Fracture.

16. The solid lyophilized vaginal dosage form of claim 1, wherein the active ingredient comprises up to 60 wt. % based on the total weight of the lyophilized dosage form.

17. The solid lyophilized vaginal dosage form of claim 1, wherein the active ingredient is selected from the group consisting of acyclovir, fluconazole, progesterone, nonoxylenol-9, terbutaline, lidocaine, testosterone, dinoprostone, *lactobacillus*, estrogen, naphthalene2-sulfonate, butoconazole, clindamycin nitrate/phosphate, neomycine sulfate, polymyxin sulfate, nystatin, clotrimazole, dextrin sulphate, glyminox, miconazole nitrate, benzalkonium chloride, sodium lauryl sulphate, tenofovir, danazol, acriflavine, leuprorelin acetate, metronidazole, benzydamine hydrochloride, chloramphenicol, oxybutynin, ethinyl estradiol, insulin, calcitonin, and salts, esters, hydrates, and solvates of any of the foregoing active ingredients that possess the same activity as the active ingredient, vaccine antigens of HIV, HPV, *Chlamydia*, Heptatits B, gonococcus and combinations thereof.

18. The solid lyophilized vaginal dosage form of claim 1, wherein the active ingredient is selected from the group consisting of antibacterial agents, antifungal agents, antiprotozoal agents, antiviral agents, labor-inducing agents, spermicidal agents, prostaglandins, steroids and microbicides, proteins/peptides, vaccine antigens and combinations thereof.

19. The solid lyophilized vaginal dosage form of claim 1, further comprising silicon dioxide.

20. The solid lyophilized vaginal dosage form of claim 1, wherein the crystalline structure forming agent comprises mannitol.

21. A method of delivering an active ingredient to a vaginal cavity comprising the step of contacting the solid lyophilized vaginal dosage form as claimed in claim 1 with the vaginal mucosa.

* * * * *